United States Patent
Oku et al.

(10) Patent No.: US 7,132,579 B2
(45) Date of Patent: Nov. 7, 2006

(54) METHOD OF CHLORINE PURIFICATION AND PROCESS FOR PRODUCING 1,2-DICHLOROETHANE

(75) Inventors: Noriaki Oku, Ichihara (JP); Tateo Seo, Chiba (JP); Kiyoshi Iwanaga, Chiba (JP)

(73) Assignee: Sumitomo Chemical Company, Limited, Osaka (JP)

( * ) Notice: Subject to any disclaimer, the term of this patent is extended or adjusted under 35 U.S.C. 154(b) by 307 days.

(21) Appl. No.: 10/480,279

(22) PCT Filed: Jun. 20, 2002

(86) PCT No.: PCT/JP02/06172

§ 371 (c)(1),
(2), (4) Date: Dec. 11, 2003

(87) PCT Pub. No.: WO03/002453

PCT Pub. Date: Jan. 9, 2003

(65) Prior Publication Data

US 2004/0179987 A1    Sep. 16, 2004

(30) Foreign Application Priority Data

Jun. 28, 2001  (JP) .............................. 2001-196168
Jun. 28, 2001  (JP) .............................. 2001-196169

(51) Int. Cl.
*C07C 17/38* (2006.01)
*B01D 61/00* (2006.01)

(52) U.S. Cl. ..................... 570/262; 210/755; 210/754; 210/753; 210/750; 210/740; 210/767

(58) Field of Classification Search ................ 570/262; 210/755, 754, 753, 750, 740, 767
See application file for complete search history.

(56) References Cited

U.S. PATENT DOCUMENTS 4,554,392 A    11/1985   Leuck et al.
4,873,384 A    10/1989   Wachi et al.

FOREIGN PATENT DOCUMENTS

| JP | 58-92626 |  | 6/1983 |
|----|----------|---|--------|
| JP | 58-177923 |  | 10/1983 |
| JP | 58-208104 | A | 12/1983 |
| JP | 61-268635 |  | 11/1986 |
| JP | 02-137704 | A | 5/1990 |
| JP | 5-9137 |  | 1/1993 |
| JP | 09-025248 | A | 1/1997 |
| JP | 2000-272906 | A | 10/2000 |

*Primary Examiner*—Elvis O. Price
(74) *Attorney, Agent, or Firm*—Sughrue Mion, PLLC

(57) ABSTRACT

A method for chlorine purification in which crude chlorine containing nitrogen and/or oxygen is purified to separate the nitrogen and oxygen from the chloride, characterized in that the crude chlorine containing nitrogen and/or oxygen is contacted with 1,2-dichloroethane to cause the 1,2-dichloroethane to absorb the chlorine contained in the crude chlorine, and a process for producing 1,2-dichloroethane which comprises reacting ethylene with the chlorine contained in the chlorine containing 1,2-dichloroethane.

12 Claims, 5 Drawing Sheets

US 7,132,579 B2

METHOD OF CHLORINE PURIFICATION AND PROCESS FOR PRODUCING 1,2-DICHLOROETHANE

TECHNICAL FIELD

The present invention relates to a method for purifying chlorine and a process for producing 1,2-dichloroethane. More particularly, the present invention relates to a method for purifying chlorine excellent in separation efficiency, which comprises separating nitrogen and/or oxygen from crude chlorine containing nitrogen and/or oxygen, and a process for producing 1,2-dichloroethane, which comprises reacting chlorine contained in 1,2-dichloroethane containing chlorine with ethylene, and both methods are extremely advantageous ones from viewpoints of installation cost and running cost.

BACKGROUND ART

As a method for purifying chlorine, which comprises separating nitrogen and/or oxygen from crude chlorine containing nitrogen and/or oxygen, a method for separating a liquid or gas containing chlorine as a major component and a gas containing nitrogen and/or oxygen as major components by compressing and/or cooling, is illustrated, but there are problems that not only the compressing and/or cooling requires great energy, but also the installation cost is large and separation efficiency is bad.

Further, as a method for producing 1,2-dichloroethane by reacting chlorine with ethylene, for example, a method of reacting chlorine with ethylene by supplying simultaneously chlorine purified by the above-mentioned method and ethylene into 1,2-dichloroethane, is known.

DISCLOSURE OF THE INVENTION

An object of the present invention is to provide, in a method for purifying chlorine by separating nitrogen and/or oxygen from crude chlorine containing nitrogen and/or oxygen, a chlorine purification method which is excellent in separation efficiency and extremely advantageous from viewpoints of installation cost and running cost, namely, a method for purifying chlorine by separating nitrogen and/or oxygen from crude chlorine containing nitrogen and/or oxygen, wherein the method which comprises contacting crude chlorine containing nitrogen and/or oxygen with 1,2-dichloroethane to cause the 1,2-dichloroethane to absorb chlorine contained in the crude chlorine containing nitrogen and/or oxygen.

Further, another object of the present invention is to provide a method for producing 1,2-dichloroethane which is extremely advantageous from viewpoints of installation cost and running cost, namely a process for producing 1,2-dichloroethane, which comprises reacting chlorine contained in 1,2-dichloroethane containing chlorine with ethylene.

That is, the present invention is based on new findings that a difference of solubility to 1,2-dichloroethane between chlorine and nitrogen and/or oxygen, is large, and excellent separation efficiency, further suppression of installation cost and running cost can be attained by utilizing the difference.

Furthermore, other objects and advantages of the present invention will be apparent from the following descriptions.

EXPLANATION OF SYMBOLS

1. Absorbing column, 2. Cooler, 3. Reactor for producing 1,2-dichloroethane, 4. Pre-heater of 1,2-dichloroethane containing chlorine, 5. Heat exchanger for generating steam, 6. First step (step of converting hydrogen chloride into chlorine-containing gas), 7. Second step (absorbing column), 8. Third step (reactor for producing 1,2-dichloroethane), 9. Fourth step (Recycle step of 1,2-dichloroethane), 10. Fifth step (Pyrolyzer) of 1,2-dichloroethane), 11. Sixth step (step of separating vinyl chloride and hydrogen chloride, and recycling the hydrogen chloride), a. Crude chlorine containing nitrogen and/or oxygen, b, b'. 1,2-dichloroethane, c. 1,2-dichloroethane bottom liquid containing chlorine, d. Gas containing nitrogen and/or oxygen, d'. Non-condensation gas, E. Ethylene, e. 1,2-dichloroethane containing chlorine, f. Pre-heated 1,2-dichloroethane containing chlorine, g. Gas containing hydrogen chloride, h. Gas containing chlorine, i. Unabsorbed gas, j. 1,2-dichloroethane as product, k. Vinyl chloride and hydrogen chloride, l. Vinyl chloride, m. Hydrogen chloride

BEST MODE FOR CARRYING OUT THE INVENTION

As crude chlorine containing nitrogen and/or oxygen (herein-after, sometimes referred to simply as "crude chlorine") used in the present invention, crude chlorine further containing a gas such as argon, carbon dioxide, carbon mono oxide, or an organic compound, may be used.

Figure 1:
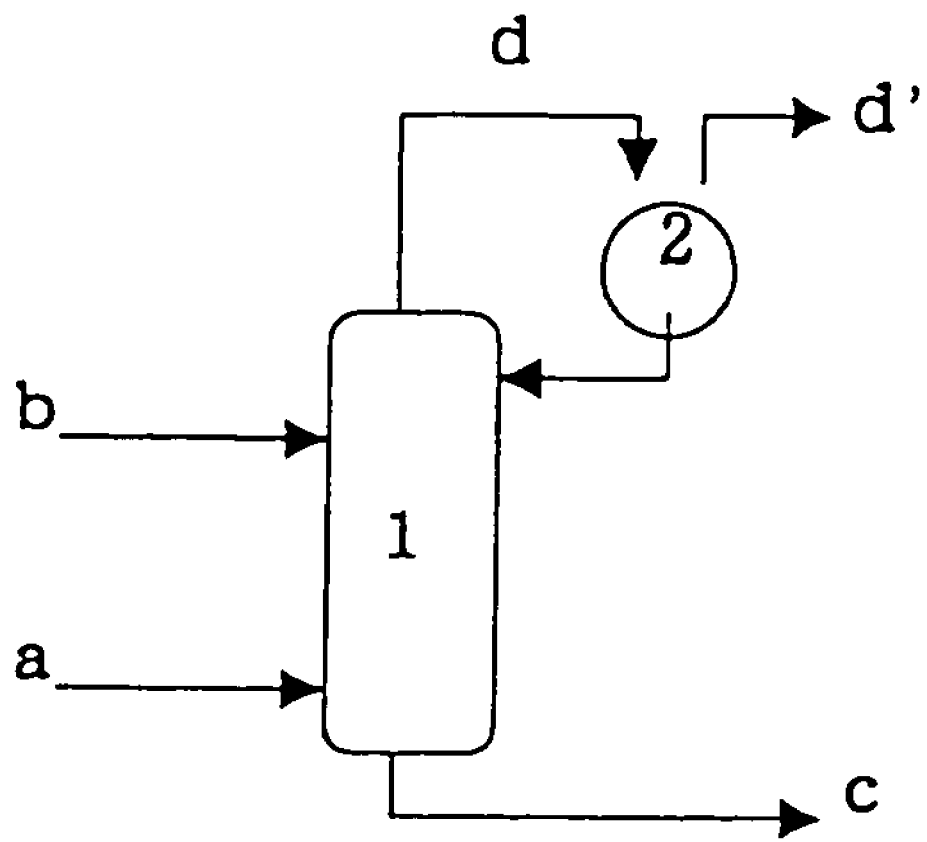
FIG. 1 shows a flow of purification of chlorine of the present invention.

In the present invention, as shown in FIG. 1, 1,2-dichloroethane containing chlorine as a bottom liquid (c) is obtained by contacting crude chlorine containing nitrogen and/or oxygen (a) with 1,2-dichloroethane (b) thereby to cause the 1,2-dichloroethane to absorb chlorine contained in the crude chlorine. Excellent separation efficiency, and further suppression of installation cost and running cost can be attained by this matter.

A contact temperature of the crude chlorine with 1,2-dichloroethane is −50 to 200° C., preferably −10 to 100° C., further preferably 0 to 100° C. When the temperature is lower than −50° C., it may become disadvantageous in economical because the installation cost becomes high. On the other hand, when higher than 200° C., chlorine may be insufficiently absorbed into 1,2-dichloroethane.

The contact is carried out under a pressure of 0.1 to 2 MPa. When the pressure is lower than 0.1 MPa, chlorine may be insufficiently absorbed into 1,2-dichloroethane, on the other hand, when higher than 2 MPa, it may become disadvantageous in economical because the installation cost becomes high.

A used amount of 1,2-dichloroethane is usually 0.1 to 200 times by weight, preferably 1 to 100 times by weigh, further preferably 1 to 50 times by weight to the amount of chlorine contained in the crude chlorine. When the amount of 1,2-dichloroethane is less than 0.1 times by weight, chlorine may be insufficiently absorbed into 1,2-dichloroethane, on the other hand, when the amount of 1,2-dichloroethane is more than 200 times by weight, it may become disadvantageous in economical because the installation cost becomes high.

After a 1,2-dichloroethane bottom liquid (c) of a column containing chlorine obtained by absorbing chlorine in the crude chlorine into 1,2-dichloroethane, is usually separated into chlorine and 1,2-dichloroethane, 1,2-dichloroethane can be recycled.

As shown in FIG. 1, a gas (d) containing nitrogen and/or oxygen not absorbed into 1,2-dichloroethane is discharged from the top of the column, but after the gas (d) is cooled with a cooler 2 to condense 1,2-dichloroethane thereby to separate from a non-condensation gas (d') for recovering 1,2-dichloroethane contained in the gas, the 1,2-dichloroethane can be recycled.

As the cooler, a heat exchanger is used, it is cooled with one stage or multi stages, and the temperature after cooled is −50 to 40° C.

A loss of 1,2-dichloroethane becomes smaller with lowering of the cooling temperature. It is preferable from viewpoints of safe operations of apparatuses to adjust concentrations of 1,2-dichloroethane in an absorbing column, a cooler, a drum, piping and the like out of the range of explosion.

In the present invention, it is preferable for improving contact efficiency to contact the crude chlorine with 1,2-dichloroethane using an absorbing column 1. It is more preferable for improving contact efficiency to use packing and plates in the absorbing column.

In the present invention, it is preferable to supply 1,2-dichloroethane to an upper part of a supply part of crude chlorine of the absorbing column.

In the present invention, it is preferable to use crude chlorine containing nitrogen and/or oxygen obtained by a catalytic oxidation and/or electrolysis of hydrogen chloride.

Among these, it is preferable to use crude chlorine containing nitrogen and/or oxygen obtained by oxidizing hydrogen chloride with an oxygen-containing gas in the presence of a catalyst containing ruthenium oxide.

Next, a process for producing 1,2-dichloroethane by reacting chlorine contained in 1,2-dichloroethane containing chlorine with ethylene, is described in detail.

Figure 2:
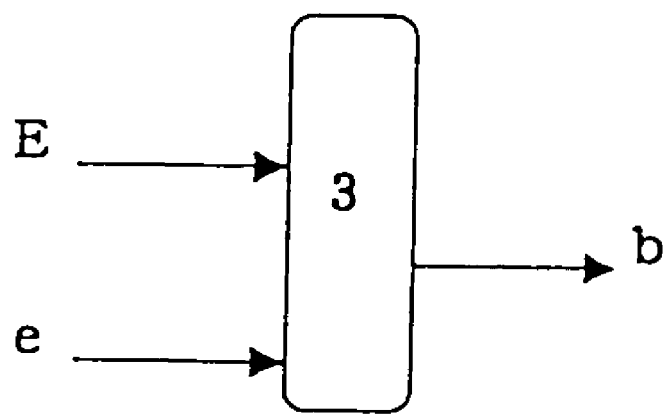
FIG. 2 shows a flow of an example of production of 1,2-dichloroethane.

In the present invention, as shown in FIG. 2, chlorine contained in 1,2-dichloroethane containing chlorine (e) is reacted with ethylene (E) in a reactor 3.

A chlorine concentration in the 1,2-dichloroethane containing chlorine is 0.01% by weight or more, preferably 0.1% by weight or more, more preferably 1% by weight or more. When the chlorine concentration is less than 0.01% by weight, it may becomes disadvantageous in economical because the installation costs become high. The upper limit of the concentration is a saturated concentration thereof, and can be determined by temperature and pressure.

As a method of reacting chlorine in 1,2-dichloroethane containing chlorine with ethylene, a fixed bed flow method, fluidized bed flow method or homogenous system flow method is given, and can be carried out in both of a liquid phase and gas phase. For example, in a case of the liquid phase, it can be carried out by dissolving a catalyst in 1,2-dichloroethane produced. It is carried out under a pressure of 0.1 to 5 MPa. It is carried out at a temperature of 0 to 500° C., preferably 20 to 300° C., more preferably 20 to 200° C.

When chlorine in 1,2-dichloroethane is reacted with ethylene, another chlorine may be fed in addition to the chlorine in 1,2-dichloroethane.

In the present invention, it is preferable from the viewpoint of suppression of running costs to conduct heat recovery of a reaction heat obtained by reacting 1,2-dichloroethane containing chlorine with ethylene (the generated heat quantity is 180 kJ per 1 mol of chlorine) as heat resources for pre-heating of 1,2-dichloroethane containing chlorine and/or ethylene, or for another process.

Figure 3:
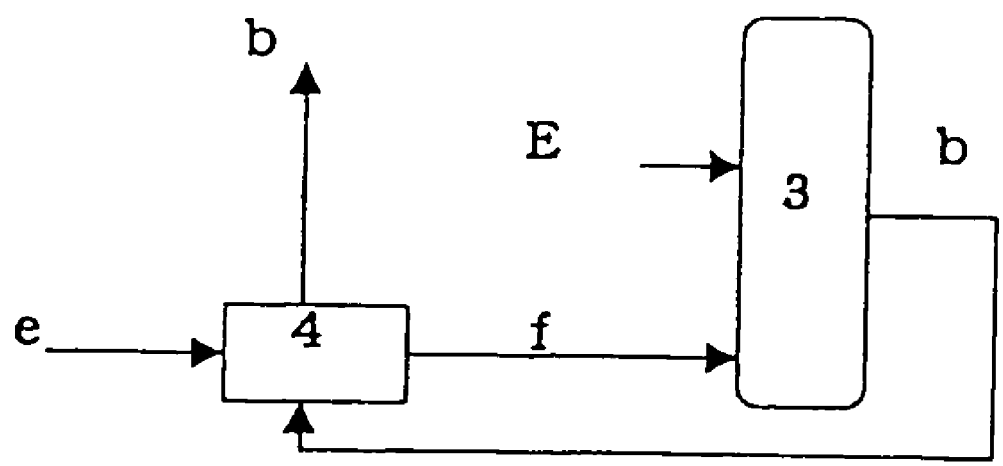
FIGS. 3 to 8 show flows of other examples of production of 1,2-dichloroethane.

For example, heat recovery can be attained by pre-heating 1,2-dichloroethane containing chlorine and/or ethylene with a reaction liquid and/or reaction gas of which the temperature has been raised by the reaction (FIG. 3).

Figure 4:
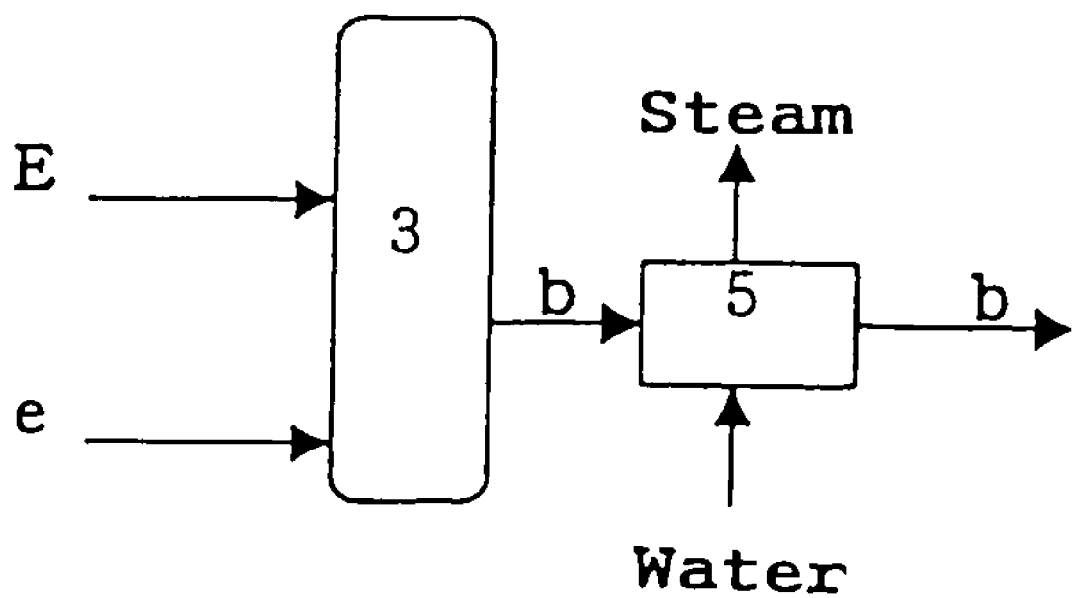

Further, it is possible to generate steam by a heat exchange with water and to recover the heat as a heat resource for another process (FIG. 4). As a heat resource for another process, for example, it can be utilized for pre-heating of a re-boiler, reactor and/or cracker in a vinyl chloride production plant or a 1,2-dichloroethane production plant.

In the present invention, it is preferable on points of raw material and installation costs that 1,2-dichloroethane containing chlorine is one obtained by contacting crude chlorine containing nitrogen and/or oxygen above-mentioned with 1,2-dichloroethane. Further, it is preferable that 1,2-dichloroethane is one obtained by reacting chlorine contained in 1,2-dichloroethane containing chlorine with ethylene.

Figure 5:
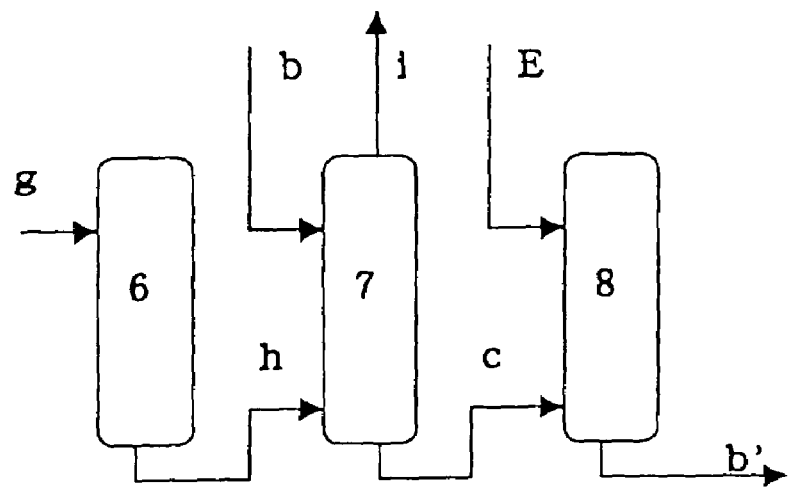

Furthermore, another embodiment of 1,2-dichloroethane production is described using FIG. 5.

First, in the first step 6, hydrogen chloride in a hydrogen chloride-containing gas (g) is converted into a chlorine-containing gas (h). As hydrogen chloride, any hydrogen chloride-containing gas generated by pyrolysis of a chlorine compound, a reaction with phosgene, de-hydrogen chloride reaction or chlorination of an organic compound, or combustion in an incinerator, can be used.

As methods of converting hydrogen chloride into chlorine, there are listed a method of converting into a chlorine-containing gas by oxidizing hydrogen chloride with a oxygen-containing gas such as air in the presence of a catalyst and a method of converting into a chlorine-containing gas by electrolysis of hydrogen chloride. In these, a method of converting into a chlorine-containing gas by oxidizing hydrogen chloride with a oxygen-containing gas in the presence of a catalyst containing ruthenium oxide, is preferable because it can convert hydrogen chloride into chlorine at high yield.

Subsequently, in the second step 7, 1,2-dichloroethane containing chlorine (c) is obtained by contacting a chlorine-containing gas (h) obtained in the first step 6 with 1,2-dichloroethane thereby absorbing chlorine into 1,2-dichloroethane. The production of 1,2-dichloroethane is that as described above. In addition, gas not absorbed is discharged from the top of the column.

Further, it is preferable to set up, between the first step 6 and second step 7, a step of separating into a solution containing hydrogen chloride and water as main components, and a gas containing chlorine, by contacting a chlorine-containing gas (h) obtained in the first step 6 with water and/or hydrochloric acid, and/or a step of removing water in the chlorine-containing gas.

In the third step 8, 1,2-dichloroethane (b') is obtained by reacting chlorine contained in 1,2-dichloroethane containing chlorine (c) obtained in the second step 7 with ethylene.

The method of reacting chlorine in 1,2-dichloroethane containing chlorine (c) with ethylene is as described above.

Figure 6:
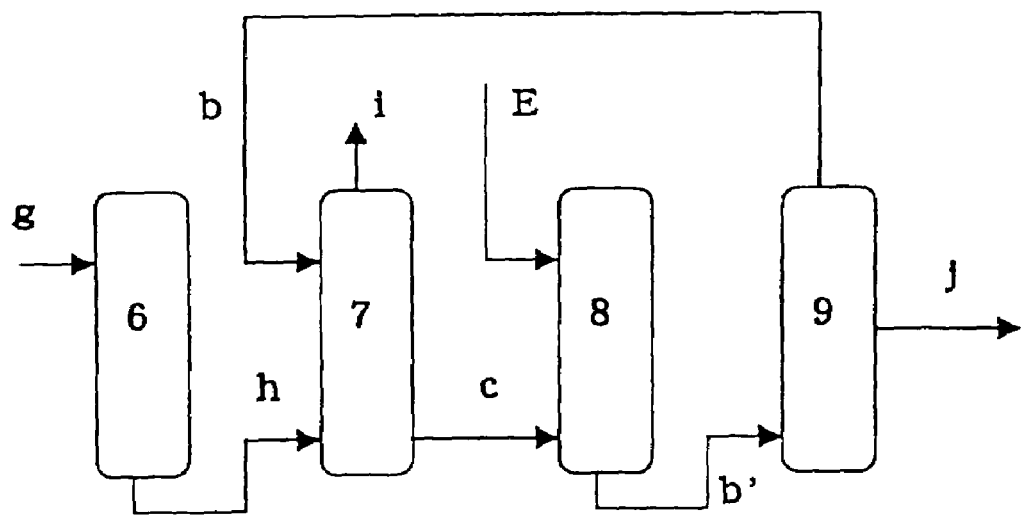

Moreover, in the embodiment of the present invention, it is preferable to set up a fourth step 9 in addition to the first, second and third steps (FIG. 6).

The fourth step 9 is a step for feeding a part of 1,2-dichloroethane obtained in the third step 8 into the second step 7 for recycling, and getting the remained 1,2-dichloroethane as product (j).

Figure 7:
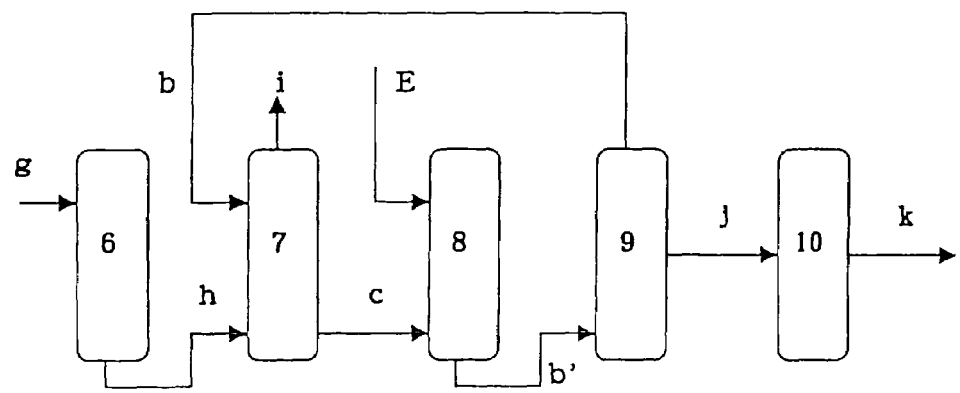

Furthermore, in FIG. 7, a step (fifth step 10) of obtaining vinyl chloride and hydrogen chloride (k) by pyrolysis of 1,2-dichloroethane as product (j) obtained in the fourth step 9, is added, and there is an advantage that recycle of hydrogen chloride produced by pyrolysis is possible in addition to advantages described above.

Figure 8:
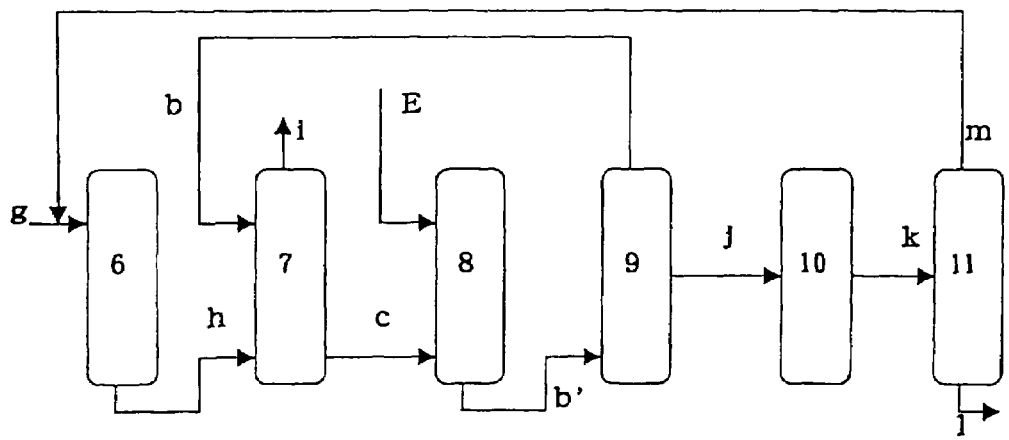

Moreover, in FIG. 8, as a sixth step 11, a step of separating (k) obtained in the fifth step 10 into vinyl chloride (l) and hydrogen chloride (m), and feeding hydrogen chloride (m) into the first step 6 for recycling, is added. According to this process, a process for producing vinyl chloride; containing the purification step of chlorine containing contacting of the chlorine-containing gas with 1,2-dichloroethane as described above and the step of producing 1,2-dichloroethane by reacting chlorine in 1,2-dichloroethane containing chlorine with ethylene; and further using hydrogen chloride as a starting material which can be recycled, can be also preferably provided.

EXAMPLE

The present invention is described by Examples below.

Example 1

As shown by the flow of FIG. 1, when 60 t/hr of crude chlorine (a) containing nitrogen and oxygen having a composition shown in Table 1, and 300 t/hr of 1,2-dichloroethane (b) are continuously fed into an absorbing column 1 having a theoretical plate number of 10 equipped with a cooler 2, and contacted under conditions of a pressure of the top of the column of 0.5 MPa, a temperature of the top of the column of 5° C., and a temperature of the bottom of the column of 18° C. to obtain 320 t/hr of 1,2-dichloroethane (c) containing chlorine having a composition shown in Table 1 as a bottom liquid. From the cooler 2 of the top of the column, 40 t/hr of a non-condensation gas component (d') having a composition shown in Table 1 is obtained.

TABLE 1

| Components | a | b | c | d' |
|---|---|---|---|---|
| Chlorine | 34.0 | — | 6.3 | 1.0 |
| Nitrogen | 56.7 | — | 0.1 | 84.2 |
| Oxygen | 9.3 | — | <0.1 | 14.0 |
| 1,2-dichloroethane | — | >99 | 93.6 | 0.8 |

(Unit: % by weight)

Example 2

When into a reactor 3 shown in FIG. 2, 100 t/hr of a liquid (e) having a composition composed of 0.1% by weight of nitrogen, 94% by weight of 1,2-dichloroethane and 5.9% by weight of chlorine, and 2.3 t/hr of ethylene (E) are continuously fed, and these are contacted under conditions of a pressure of 0.3 MPa and a temperature of 100° C. (conversion: 100%), 1,2-dichloroethane (b) having a chlorine content of less than 0.01% by weight is obtained.

Example 3

Into a pre-heater 4 shown in FIG. 3, 100 t/hr of a liquid (e) (20° C.) having a composition composed of 1% by weight of nitrogen, 90% by weight of 1,2-dichloroethane and 9% by weight of chlorine, and 104 t/hr of 1,2-dichloroethane (b) (100° C.) having a chlorine concentration of less than 0.01% by weight obtained in a reactor 3, are continuously fed. By an indirect heat exchange in the pre-heater 4, 1,2-dichloroethane (b) becomes 40° C. in temperature, and is continuously discharged to out of the system. A liquid (f) heated to 80° C. is obtained and is continuously fed into a reactor 3. Simultaneously, ethylene (E) is continuously fed at 4 t/hr into the reactor 3 and is contacted under conditions of a pressure of 0.3 MPa and a temperature of 100° C. to obtain 1,2-dichloroethane (b) having a chlorine concentration of less than 0.01% by weight. As described above, a continuous system for heat recovery in which a part or all of heat generated in the reactor 3 is used for pre-heating of (e) through the pre-heater 4, is possible.

Example 4

Into a reactor 3 shown in FIG. 4, 100 t/hr of a liquid (e) having a composition composed of 1% by weight of nitrogen, 90% by weight of 1,2-dichloroethane and 9% by weight of chlorine, and 4 t/hr of ethylene (E) are continuously fed and contacted under conditions of a pressure of 0.4 MPa and a temperature of 100° C., 1,2-dichloroethane (b) (135° C.) having a chlorine content of less than 0.01% by weight is obtained.

Subsequently, when 104 t/hr of (b) (135° C.) and 4 t/hr of water (20° C.) are continuously fed into a heat exchanger for generating steam 5, to utilize a heat generated by condensation of 1,2-dichloroethane (b) and to carry out indirect heat exchange for generating steam from water, steam (125° C.) is generated and continuously discharged out of the system.

As described above, a continuous system for heat recovery in which a part or all of heat generated in the reactor 3 is recovered as steam through the heat exchanger for generating steam 5, is possible.

Example 5

As shown by a flow of FIG. 5, when, into the sixth step of converting hydrogen chloride into chlorine-containing gas, 10.6 kg/hr of a gas (g) containing nitrogen, oxygen and hydrogen chloride having a composition shown in Table 2 is continuously fed to carry out a reaction under a pressure of 0.6 MPa at a temperature of 300 to 380° C. in the presence of a catalyst under a conversion of 85%, and unreacted hydrogen chloride and water produced from the obtained gas is separated and dried, 9.2 kg/hr of chlorine containing gas (h) having a composition shown in Table 2 is obtained. Subsequently, when chlorine-containing gas (h) is continuously fed into an absorbing column 7, simultaneously, 100 kg/hr of 1,2-dichloroethane (b) is continuously fed to contact them under conditions of a pressure of the top of the column of 0.5 MPa, a temperature of the top of the column of 5° C., a temperature of the bottom of the column of 18° C., a gas (i) not absorbed having a composition shown in Table 2 is obtained from the top of the column, and 1,2-dichloroethane (c) containing chlorine having a composition shown in Table 2 is obtained as a bottom liquid. Subsequently, when, into a reactor 8 for producing 1,2-dichloroethane, the bottom liquid of 1,2-dichloroethane (c) containing chlorine obtained from the bottom of the absorbing column 7 is continuously fed, simultaneously, 1.5 kg/hr of ethylene (E) is continuously fed, and conditions are adjusted at a pressure of 0.3 MPa and temperature of 120° C., chlorine in the bottom liquid of 1,2-dichloroethane (c) containing chlorine, is converted into 1,2-dichloroethane to obtain 1,2-dichloroethane (b'). A composition of each of streams is shown in Table 2.

TABLE 2

|  | g | h | b | i | c | b' |
|---|---|---|---|---|---|---|
| Component |  |  |  |  |  |  |
| Hydrogen chloride | 36.6 | — | — | — | — | — |
| Chlorine | — | 34.9 | — | — | 3.1 | — |
| Nitrogen | 48.2 | 55.6 | — | 85.0 | — | — |
| Oxygen | 15.1 | 9.6 | — | 15.0 | — | — |
| 1,2-dichioroethane | — | — | >99 | — | 96.9 | >99 |

Example 6

As shown by a flow of FIG. 7, when 1,2-dichloroethane (b') obtained by the same method as in Example 5 is continuously fed into the step 9 of recycle of 1,2-dichloroethane and a part of them is recycled to an absorbing column 7 as 1,2-dichloroethane (b), 1,2-dichloroethane as product (j) is obtained. Subsequently, when 1,2-dichloroethane as product (j) is continuously fed into a pyrolyzer of 1,2-dichloroethane 10, vinyl chloride and hydrogen chloride (k) is obtained. A composition of each of streams is shown in Table 3.

TABLE 3

|  | g | h | b | i | c | b' | j | k |
|---|---|---|---|---|---|---|---|---|
| Component |  |  |  |  |  |  |  | — |
| Hydrogen chloride | 36.6 | — | — | — | — | — | — | 36.9 |
| Chlorine | — | 34.9 | — | — | 3.1 | — | — | — |
| Nitrogen | 48.2 | 55.6 | — | 85.0 | — | — | — | — |
| Oxygen | 15.1 | 9.6 | — | 15.0 | — | — | — | — |
| 1,2-dichloroethane | — | — | >99 | — | 96.9 | >99 | >99 | — |
| Vinyl chloride | — | — | — | — | — | — | — | 63.1 |

(Unit: % by weight)

INDUSTRIAL APPLICABILITY

As described above, according to the present invention, there can be provided, in a method for purifying chlorine by separating nitrogen and/or oxygen from crude chlorine containing nitrogen and/or oxygen, a method for purifying chlorine, which comprises contacting crude chlorine containing nitrogen and/or oxygen with 1,2-dichloroethane thereby allowing to absorb chlorine in crude chlorine; and a method for producing 1,2-dichloroethane, which comprises reacting chlorine in 1,2-dichloroethane containing chlorine with ethylene. In addition, these methods can be used as a step in vinyl chloride production in which hydrogen chloride is used as a starting material which is capable of recycling.

The invention claimed is:

1. A method for purifying chlorine which comprises separating nitrogen and/or oxygen from crude chlorine containing nitrogen and/or oxygen, wherein the method comprising contacting the crude chlorine containing nitrogen and/or oxygen with 1,2-dichloroethane thereby allowing to absorb chlorine in the crude chlorine containing nitrogen and/or oxygen into 1,2-dichloroethane.

2. The method for purifying chlorine according to claim 1, which comprises feeding the crude chlorine containing nitrogen and/or oxygen and 1,2-dichloroethane into an absorbing column to contact them.

3. The method for purifying chlorine according to claim 2, wherein 1,2-dichloroethane is supplied to an upper part of a supply part of the absorbing column to which the crude chlorine containing nitrogen and/or oxygen is supplied.

4. The method for purifying chlorine according to claim 2, wherein the crude chlorine containing nitrogen and/or oxygen is one obtained by catalytic oxidation and/or electrolysis of hydrogen chloride.

5. A process for producing 1,2-dichloroethane, which comprise:
   contacting crude chlorine containing nitrogen and/or oxygen with 1,2-dichloroethane thereby making chlorine in the crude chlorine containing nitrogen and/or oxygen to absorb in the 1,2-dichloroethane and separating nitrogen and/or oxygen from the crude chlorine containing nitrogen and/or oxygen, and then
   reacting the chlorine in the 1,2-dichloroethane with ethylene.

6. The process for producing 1,2-dichloroethane according to claim 5, which further comprises a step of heat recovery in which a reaction liquid and/or reaction gas of which the temperature has been raised by heat obtained by reaction of chlorine in 1,2-dichloroethane containing chlorine with ethylene is used for pre-heating 1,2-dichloroethane containing chlorine and/or ethylene, and/or as a heat resource for another process.

7. The process for producing 1,2-dichloroethane according to claim 5, wherein 1,2-dichloroethane used for allowing to contain chlorine is one obtained by reacting chlorine in 1,2-dichloroethane containing chlorine with ethylene.

8. A process for producing 1,2-dichloroethane, which comprises the following steps:
   first step; a step of obtaining crude chlorine containing nitrogen and/or oxygen by subjecting hydrogen chloride to electrolysis and/or catalytic oxidation,
   second step; a step of obtaining 1,2-dichloroethane containing chlorine by contacting the crude chlorine containing nitrogen and/or oxygen with 1,2-dichloroethane thereby making chlorine in the crude chlorine containing nitrogen and/or oxygen to absorb in the 1,2-dichloroethane and separating nitrogen and/or oxygen from the crude chlorine containing nitrogen and/or oxygen, and
   third step; a step of obtaining 1,2-dichloroethane by reacting chlorine in the 1,2-dichloroethane containing chlorine obtained in the second step with ethylene.

9. The process for producing 1,2-dichloroethane according to claim 8, wherein the crude chlorine obtained in the first step is one obtained by oxidizing hydrogen chloride with a oxygen-containing gas in the presence of a catalyst.

10. The process for producing 1,2-dichloroethane according to claim 8 or 9, which further comprises the following step:
    fourth step; a step of feeding a part of 1,2-dichloroethane obtained in the third step into the second step for recycling, and getting the remained 1,2-dichloroethane as a product.

11. The process for producing 1,2-dichloroethane according to claim 10, which further comprises the following step:

fifth step; a step of pyrolyzing 1,2-dichloroethane as a product obtained in the fourth step into vinyl chloride and hydrogen chloride.

12. The process for producing 1,2-dichloroethane according to claim 11, which further comprises the following step:

Sixth step; a step of separating vinyl chloride and hydrogen chloride obtained in the fifth step, then recycling the hydrogen chloride into the first step.

* * * * *